United States Patent [19]

Rieke

[11] Patent Number: 5,490,951
[45] Date of Patent: Feb. 13, 1996

[54] HIGHLY REACTIVE FORM OF COPPER AND REAGENTS THEREOF

[75] Inventor: Reuben D. Rieke, Lincoln, Nebr.

[73] Assignee: University of Nebraska, Nebr.

[21] Appl. No.: 43,143

[22] Filed: Mar. 23, 1993

Related U.S. Application Data

[63] Continuation of Ser. No. 692,236, Apr. 26, 1991, abandoned.

[51] Int. Cl.$^6$ .............................. C09K 3/00; B01J 23/72
[52] U.S. Cl. ............................. 252/182.33; 252/182.12; 502/345
[58] Field of Search ..................... 252/182.12, 182.33; 502/345

[56] References Cited

U.S. PATENT DOCUMENTS

| | | | |
|---|---|---|---|
| 3,948,803 | 4/1976 | Carney | 585/462 |
| 4,152,303 | 5/1979 | Cohen et al. | 252/474 |
| 4,687,877 | 8/1987 | Bartley et al. | 502/345 |

OTHER PUBLICATIONS

R. D. Rieke, Abstract of National Institute of Health Grant No. GM35153.
R. M. Wehmeyer, "the Preparation and Chemistry of Active Copper, Nickel, and Zinc", Ph.D. Thesis, The University of Nebraska–Lincoln (1988).
R. D. Rieke et al., *J. Org. Chem.*, 44, 3445–3446 (1979).
R. D. Rieke, *Energy Res. Abstr*, 10(18), Abstr. No. 37255 (1985) (Report No. DOE/ER/10603–T3).
R. D. Rieke et al., Paper entitled "Direct formation of functionalized organocopper reagents from highly reactive copper and alkyl halides" (Abstract No. 306), presented at American Chemical Society 196th National Meeting, Los Angeles, CA, Sep. 25–30, 1988.
R. D. Rieke, *Science*, 246, 1260–1264 (1989).
R. M. Wehmeyer et al., *J. Org. Chem.*, 52, 5056–5057 (1987).
T.–C. Wu et al., *J. Org. Chem.*, 55, 5045–5051 (1990).
L. Zhu et al., *Tetrahedron Letters*, 32, 2865–2866 (1991).
L. Zhu et al., *J. Org. Chem.*, 56, 1445–1453 (1991).
A. Alexakis et al., *Tetrahedron Lett.*, 27, 1047 (1986).
E. J. Corey et al., *Tetrahedron Lett.*, 26 6015 (1985).
E. J. Corey et al., *Tetrahedron Lett.*, 26, 6019 (1985).
G. W. Ebert et al., *J. Org. Chem.*, 49, 5280 (1984).
G. W. Ebert et al., *J. Org. Chem.*, 53, 4482 (1988).
B. H. Lipshutz et al., *J. Org. Chem.*, 54, 4977 (1989).
B. H. Lipshutz et al., *J. Am. Chem. Soc.*, 112, 4063 (1990).
B. H. Lipshutz et al., *J. Am. Chem. Soc.*, 112, 4404 (1990).
The Merck Index, 10th Ed., Merck & Co. Pub. 1983, 7778.
R. A. O'Brien et al., *J. Org. Chem.*, 55, 788 (1990).
R. D. Rieke et al., *High Energy Processes in Organometallic Chemistry*, ACS Symposium Series No. 333, ACS 1987, Ch. 14, 223.
R. D. Rieke et al., *Synth. Commun.*, 19, 1833 (1989).
R. D. Rieke et al., *Tetrahedron*, 45, 443 (1989).
R. D. Rieke et al., *Synth. Commun.*, 20, 2711 (1990).
D. E. Stack et al., *J. Am. Chem. Soc.*, 113, 4672 (1991).
K. Takeda et al., *Bull. Chem. Soc. Jpn.*, 41, 268 (1968).
R. M. Wehmeyer et al., *Tetrahedron Letters*, 29, 4513 (1988).
T.–C. Wu et al., *J. Org. Chem.*, 52, 5057 (1987).
T.–C. Wu et al., *J. Org. Chem.*, 53, 2381 (1988).
T.–C. Wu et al., *Tetrahedron Letters*, 29, 6753 (1988).

*Primary Examiner*—Edward A. Miller
*Attorney, Agent, or Firm*—Merchant, Gould, Smith, Edell, Welter, & Schmidt

[57] ABSTRACT

A novel zerovalent copper species and an organocopper reagent are disclosed. The zerovalent copper species is directly produced by reaction of a reducing agent with a combination of copper(I) cyanide or halide and an alkali metal halide salt. The organocopper reagent resulting from the reaction of the zerovalent copper species and an organic compound having one or more stable anionic leaving groups is a stable reagent that will not significantly homocouple and under controlled conditions tolerates the presence of nitrile, epoxide, imine, enone, ketone, ester, allyl and benzyl groups within the organo radical. The reagent can be controlled so that it will selectively add to an organic electrophile such as an acid halide or aldehyde while other less reactive electrophilic groups are present. The reagent will also add under controlled conditions to epoxide, enone, imine and ketone groups.

10 Claims, No Drawings

HIGHLY REACTIVE FORM OF COPPER AND REAGENTS THEREOF

The present invention was made with Government support under Contract No. GM35153 awarded by the National Institute of Health. The Government has certain rights in the invention. This is a continuation, of application Ser. No. 07/692,236, filed Apr.26, 1991, now abandoned.

BACKGROUND OF THE INVENTION

Organocopper reagents are highly desirable reagents for organic synthesis. They often react stereoselectively and do not possess the extreme nucleophilicity of such reagents as Grignard reagents. Consequently, they can be used to synthesize organic compounds that are highly functionalized.

The chemistry of allyl organocopper reagents is illustrative of this character. This reagent has received renewed interest with Lipshutz's development of higher order allylic cyanocuprates, which have been shown to be among the most reactive cuprates yet developed. See, for example, B.H. Lipshutz et al., J. Org. Chem., 54, 4977 (1989); B.H. Lipshutz et al., J. Am. Chem. Soc., 112, 4063 (1990); and B.H. Lipshutz et al., J. Am. Chem. Soc., 112, 4404 (1990).

The synthetic routes for production of organocopper reagents generally involve metathesis reactions of organolithium or Grignard reagents and accordingly cannot tolerate functionalized organic substrates. For example, the allyl organocopper reagent is obtained only by an indirect synthesis involving the transmetalation of allylic stannates with an alkylcopper reagent formed from a transmetalation of an organolithium or Grignard reagent. The problem with direct synthesis from an inorganic copper agent and an organic halide has been that the inorganic copper agent has either caused homocoupling of the organohalides or the zerovalent copper reagent would not undergo oxidative addition with the organic halide.

An organocopper reagent can be produced directly from a highly reactive form of zerovalent copper which is obtained from the reduction of copper(I) iodide phosphine complexes with a solution of lithium naphthalenide in tetrahydrofuran under argon. See, for example, R.D. Rieke et al., Tetrahedron, 45, 443 (1989); and R.D. Rieke et al., Synth. Commun., 20, 2711 (1990). The active copper produced by this method will undergo oxidative addition to primary bromides, vinyl iodides, vinyl bromides, as well as aryl iodides and bromides The organic halides can contain a limited number of functional groups such as esters, nitriles, and chlorides. The resulting organocopper reagents undergo the typical known lower order and higher order cuprate additions with electrophiles. Moreover, in the presence of the phosphine byproduct represents a severe complication for product purification.

Therefore, an object of the invention is to produce a zerovalent copper reagent which is more reactive than that obtained with the copper(I) iodide phosphine method. A further object is the development of a zerovalent copper reagent that is free of phosphines. Another object is the direct production of highly functionalized aryl and alkyl cuprates from the corresponding halides and highly functionalized allyl cupwates from the corresponding halides and acetates. Yet another object is the production of bis- and tris-organocopper reagents by direct synthesis from zerovalent copper metal and organic compounds having two or more halogens.

SUMMARY OF THE INVENTION

These and other objects are achieved by the present invention which is directed to a new zerovalent copper species, a new organocopper reagent and synthetic reactions performed with this organocopper reagent.

The zerovalent copper species is composed of zerovalent copper metal atoms in mixture or combination with an alkali metal salt of a halide or cyanide or both, preferably both. The species is formed from the reduction of a complex of copper(I) cyanide or halide, preferably cyanide, and an alkali metal salt of a halide with a reducing agent having a reduction potential of at least about 100 mV more negative than that of copper(I). The zerovalent copper species is suspendable in an ethereal, polyethereal or hydrocarbon solvent such as ethyl ether, tetrahydrofuran, glyme, diglyme, benzene and the like.

The organocopper reagent is a mixture or combination of an organic cuprate and an alkali metal salt of cyanide, halide or both. The organic cuprate is an aliphatic, aryl, arylalkyl, heterocyclic or polymeric mono- or poly- cuprate formed by reaction of the copper of the zerovalent copper species with an aliphatic, aryl, arylalkyl, heterocyclic or polymeric compound having one or more stable anionic leaving groups such as halide. The aliphatic, aryl, arylalkyl or polymeric group of this reagent may optionally be functionalized with such compatible groups as olefin, ester, ketone, enone, epoxide, amide, ether and nitrile. In the context of this invention, the term "aliphatic" means a saturated or unsaturated linear, branched or cyclic hydrocarbon radical the term "heterocyclic" means a mono or polynuclear cyclic radical containing carbons and one or more heteroatoms such as nitrogen, oxygen or sulfur or a combination thereof in the ring or rings, including but not limited to pyridine, pyrrole, indole, thiazole, pyrazine, guanine, cytosine, thymine, adenine, uredine, uracil, oxazole, pyrazole, hydantoin, piperazine, quinoline, xanthene, acidine; the term "aryl" means a mono or polynuclear aromatic hydrocarbon radical; the term "arylalkyl" means a linear, branched or cyclic alkyl hydrocarbon radical having a mono or polynuclear aromatic hydrocarbon or heterocyclic substituent; and the term "polymeric" means a polyolefin, polyester, polyurethane, polyamide, polycarbonate, or polyether.

The organocopper reagent is reactive with a wide variety of organic electrophiles containing groups such as carboxylic acid halides, aldehydes, ketones, epoxides, enones and imines. This reactivity is selective so that some of these electrophilic groups are preferred over others. In particular, depending upon the control of thermal conditions and stoichiometry, the organocopper reagent will selectively react with a carboxylic acid halide group in the presence of the other foregoing electrophilic groups. This selection is obtained at a very low temperature. At moderately low temperatures, the organocopper reagent will also react with aldehyde groups in the presence of epoxide, enone, ketone and imine groups. At slightly higher temperatures, the organocopper reagent will react with epoxide, enone and imine groups. At moderate temperatures, the organocopper reagent will react with ketone groups. The organocopper reagent will not readily react with ethers, esters or nitrile groups. Thus, the organocopper reagent provides a direct route to difficult-to-make functionalized compounds as well as to heretofore unavailable compounds.

In preferred embodiments, the copper species is a combination of zerovalent copper metal atoms and lithium cyanide and lithium bromide or chloride, the organocopper reagent formed from the oxidative addition of an aliphatic chloride or acetate, preferably an allylic chloride or acetate, and the organocopper reagent can be selectively coupled with an imine, epoxide, enone, ketone, aldehyde or acid halide. Product isolation has been greatly simplified by this new phosphine-free reagent.

DETAILED DESCRIPTION OF THE INVENTION

The present invention is based upon the discovery of a zerovalent copper metal species that displays surprising and unexpected reactivity toward aliphatic, aryl, heterocyclic, arylalkyl and polymeric mono- or poly- halides (hereinafter organic halides). It is believed that the copper species is a cluster of copper atoms associated in some manner with the alkali metal salts provided by (a) the coordinate complexing agent for the copper salt starting material and (b) the salt produced from the cation of the reducing agent and the anion of the copper salt starting material. The cluster-salt association is most likely a surface phenomenon and is believed to facilitate the oxidative transfer reaction between the copper species and the organic halides without substantial homocoupling and without indiscriminate reaction with other electrophilic functional groups.

Notwithstanding these theoretical considerations, the zerovalent copper species of this invention is highly dispersed at low temperature and will react with organic halides at low temperature to produce selectively reactive organic cuprates.

The Zerovalent Copper Species

The zerovalent copper species is a mixture or combination of copper metal atoms and an alkali metal salt of a halide, cyanide or both. Preferably, the alkali metal salt of cyanide or cyanide and halides is present. The mixture or combination is highly dispersible in ethereal, polyethereal or hydrocarbon solvent.

The zerovalent copper species can be produced by reaction of a reducing agent with a starting material complex of copper cyanide or halide, preferably cyanide, and an alkali metal salt of a halide. It is especially preferred that copper cyanide be present in the complex. The halide of the salt (and the copper halide when used) may be F, Cl, Br, I; preferably Cl or Br. The alkali metal of the salt may be Li, Na, K, Rb, Cs; preferably Li, Na or K, most preferably Li. reagent that has a reduction potential at least 100 mV more negative than that of copper(I). Any reducing agent having a reduction potential of +0.90 mV will satisfy this relation. Examples include alkali and alkali earth metals, alkali and alkali earth metal salts of aromatic anions, such salts being, for instance, sodium or lithium naphthalide, biphenylide or anthracenylide; metal hydrides such as lithium aluminum hydride, sodium borohydride, sodium hydride, metal intercalated graphites and alkali metals dissolved in glymes or ethers.

The process for reduction to produce the zerovalent copper species is conducted under conditions designed to prevent its reoxidation. Generally, these conditions include use of nonhydroxylic solvents and the exclusion of oxygen. Also, the conditions are controlled so as to promote the existence of the copper atoms as small clusters and to avoid their agglomeration into larger configurations. Preferably, these conditions include low temperatures of preferably less that $-60°$ C., an inert atmosphere, and an ether or polyether solvent such as diethyl ether, dimethyl ether, tetrahydrofuran and the like. The starting material complex is soluble or highly dispersible in the solvent at this low temperature. The reduction can as well be conducted in a hydrocarbon solvent with N,N,N',N'-tetramethyl-ethylenediamine (TMEDA) to solubilize or disperse the starting material complexe and reducing agent.

Although the copper species can be maintained for a time under these conditions, it is also quite reactive. Consequently, it is preferably synthesized immediately before use.

The Organocopper Reagent

Generally, the organocopper reagent of this invention is a mixture or combination of an aliphatic, aryl, heterocyclic, arylalkyl or polymeric mono- or poly- cuprate (hereinafter organic cuprate) and alkali metal salts. The cuprate moiety and alkali metal salts are derived from the foregoing zerovalent copper species. It is believed that as occurs in the precursor copper species, the cuprate moiety or moieties of the organic cuprate associate in some manner with the alkali metal salts present to form the organocopper reagent. It is further believed that this association is in part responsible for the novel and selective reactivity of the organocopper reagent of this invention.

The organocopper reagent is produced by reaction of the zerovalent copper species with an aliphatic, aryl, heterocyclic, arylalkyl or polymeric compound having one or more stable anionic leaving groups such as halide or alkylcarbonyloxy, preferably halide. The copper species undergoes an oxidative transfer with the anionic leaving group or groups to form the cuprate moiety. If more than one leaving group of the same kind is present, the copper species will generally react first with leaving groups bound to sp3 carbons, second with those bound to sp2 carbons. If multiple leaving groups are present, the zerovalent copper species will react with all leaving group sites in the foregoing order until the species is completely consumed. The reaction is generally conducted under conditions designed to preserve the integrity of the organocopper reagent, those conditions including, for example, the exclusion of water and oxygen. Preferably, the conditions also include low temperature such as less than about $-60°$ C.

Generally, the organic group of the organic cuprate may be any saturated, olefinically unsaturated or aromatic hydrocarbon or a heterocycle containing carbon, nitrogen, oxygen, sulfur or combinations thereof in the heteronucleus, or the functionalized derivatives thereof, or a polymer based upon ethylenyl, ester, amide, urethane, carbonate or ether units or the functionalized derivatives thereof. The molecular size may range from organic compounds and monomers, typically having from 1 to about 300 carbons, to polymeric compounds having molecular weights up to and including the million range. Preferred aliphatic, aryl, heterocyclic and arylalkyl groups include linear or branched alkyl, cycloalkyl, allyl, vinyl, phenyl, benzyl, pyridyl, quinolinyl, piperadinyl, cytosinyl, uracinyl, guaninyl, adenosinyl, pyrrolyl, thiazolyl, the methylenyl derivatives of such heterocycles and phenyl alkyl groups as well as the hydrocarbon substituted and/or functionalized forms thereof. The hydrocarbon substituents may be one or more of such groups as alkyl, cycloalkyl, heterocyclic, olefinic and aromatic groups as well as combinations thereof, each substituent having from 1 to about 30 carbons. The substituent or substituents are bound to aliphatic, aromatic or arylalkyl group such that they do not sterically hinder access to the leaving group. The functional group or groups may be bound to the aliphatic, aromatic or arylalkyl group and/or to the hydrocarbon substituents thereof and include such functional groups as ester, ketone, enone, epoxide, ether, amide and nitrile.

Generally, the organocopper reagent will selectively react first with carboxylic acid halide groups at very low temperatures such as less than about $-60°$ C. and under stoichiometric conditions. This reaction will selectively occur in the presence of aidehyde, ketone, enone, epoxide, imine, ether, nitrile, ester and ether groups. Under stoichiometric conditions at moderately low temperatures within a range of from about −50° C. to −30° C. and without the presence of acid halide groups, the organocopper reagent will selectively react with aldehyde groups in the presence of ketone, enone, epoxide, imine, nitrile, ether and ester groups. At slightly higher temperatures such as no less than about −20° C., the organocopper reagent will react with enone, imine and epoxide groups in the presence of ketone, either, nitrile and ester groups. At moderate temperatures within a range no less than about 0° C., the organocopper will react with ketone groups in the presence of nitrile, ether or ester groups. The organocopper reagent will also react with readily displacible organic halides at moderate temperatures. It will not, however, readily react with vinyl, ester, ether, or nitrile groups.

Although the organocopper reagent may be functionalized as outlined above, it will maintain a stable state and will not self-react as long as it is maintained within the appropriate low temperature range. It is believed that the presence of the alkali metal salts, which combine with the organic cuprate in some manner to form the organocopper reagent of this invention, contribute to this stability and selectivity. In such instances, the electrophile to be added to the organocopper reagent will have a higher affinity for the cuprate portion than does the functional moiety contained within the organic group.

Generally, the coupling reaction between the organocopper reagent and the organic electrophile is conducted in the same medium used to produce the organocopper reagent. The reaction is conducted under conditions designed to favor the production of the desired coupled product. Those conditions generally include low temperature, use of appropriate electrophiles as indicated above, addition of the electrophile to the organocopper reagent and stirring with appropriate reaction times. One or more of these conditions will be appropriate for use in particular instances. Choice of some or all of them is within the ordinary artisian's skill.

The reagents and reactions of this invention are useful in the organic synthesis of organic compounds that are difficult or impossible to prepare by other techniques. In particular, the facility to directly couple aliphatic, aryl and arylalkyl groups to organic acid halides, aldehydes or imines in the presence of other functional groups such as esters, ketones, enones, epoxides, amides, allyls and nitriles under controlled conditions enables great latitude in synthetic design. Moreover, the organocopper reagent of this invention will undergo a heretofore unknown addition to enones and epoxides. It is indeed a highly novel and unexpected discovery that allyl and similar groups can be directly coupled to acid halides and the like without the use of intermediate organolithium or Grignard compounds or phosphines. This characteristic permits the presence of many functional groups which would otherwise react with intermediate organolithium or Grignard compounds. This facility promotes the use of the reagents and reactions of this invention in the organic synthesis of highly functional pharmaceutical compounds, insecticides, herbicides, polymeric compounds, organic additives for polymer compositions, organic conductors, and organic information storage devices. Specific examples include the syntheses of prostaglandins, penicillins, tranquilizers and carbocylic anticancer agents. These syntheses are made more efficient, are economically feasible, do not involve difficult separation problems owing to the absence of phosphines. They open the synthetic and investigatory arenas to the development and use of rare or unavailable organic compounds.

PREFERRED EMBODIMENTS

The Copper Species

A preferred embodiment of the copper species is formed from a complex of copper(I) cyanide and a lithium halide. Specifically, the CuCN·2LiBr or CuCN·2LiCl complex can be reduced at low temperature such as from −100° and −110° C. to produce a zerovalent copper species that reacts with aliphatic, aryl and arylalkyl iodides, bromides, and chlorides as well as aliphatic acetates, preferably, allylic halides or acetates. The product is the organocopper reagent.

The advantage is the production of useful organocopper reagents in high yields. Furthermore, very little homocoupling of the organic halide is seen. For example, generally and preferably less than 1% homocoupling is typically observed by gas chromatography. Eliminated byproducts such as alkene are generally seen for the alkyl halides in 5–10% yield. Thus, formation of functionalized organocopper reagents containing chloride, nitrile, and ester functionalities can be conveniently produced from the inventive Cu(I) complex.

The Organocopper Reagent

Significantly, the zerovalent copper species reacts with alkyl, allylic, vinyl or phenyl halides and acetates at low temperature, such as −100° C., to produce the corresponding alkyl, allylic, vinyl, pyridyl, 2-methylenylpyridyl or phenyl organocopper reagent with less than 10% of the homocoupled byproduct.

To demonstrate the reactivity and character of this embodiment, examples of the functionalized alkyl organocopper reagents can be trapped with benzoyl chloride to produce the ketones shown in Table 1 of Example 2. These examples of organocopper reagents can also be reacted in high yield with enones to produce the 1,4 addition products as shown in Table 2 of Example 3. In another example, an allyl organocopper reagent can be reacted in high yield with benzoyl chloride to produce the beta, gamma unsaturated ketones as shown in Table 3 of Example 4.

The invention allows for the formation of unique functionalized allyl organocopper reagents by reaction of the active copper species with allyl chlorides containing a diverse range of functionality as shown in Table IV of Example 5. The active copper species can further be utilized in the formation of bis-organocopper complexes containing a variety of hybridized carbons. Subsequent reactivity can be controlled as shown in Scheme I of Example 6.

Further illustrations of the novel bis and proparyl organocopper reagents according to the invention are presented in Table V following Example 6. Intramolecular coupling can also be accomplished under appropriate controlled temperature conditions. Illustrations of such intramolecular coupling is shown in Table VI. Table VII illustrates a new class of acyl cuprate formed by reaction of a carboxylic acid halide with the zerovalent copper species according to the invention. Table VIII illustrates a new reaction for deoxygenation of sulfoxides, sulfones and sulfonates with the zerovalent copper species according to the invention. Table IX illustrates examples of heterocyclic organocopper reagents made according to the invention.

Preferred embodiments for the industrial use of the organocopper reagents of this invention are based upon the pharmaceutical arts. For example, the vinyl organocopper reagent shown below can be used in a short synthetic approach to prostanoids which are well-known pharmaceutical compounds, see The Merck Index, 10th Ed., Merck & Co. Pub. 1983, pg. 7778.

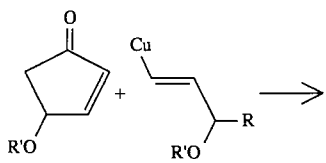

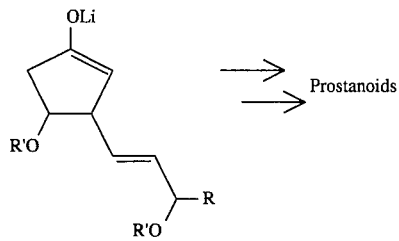

Intramolecular addition to alkynes also can provide pharmaceutical and insect behavior modification compounds. Since the organocuprates formed from oxidative addition of the active copper species to organohalides can tolerate significant functionality, acetylenes can be incorporated into the organohalides used. This incorporation would allow for the intramolecular addition of an organocuprate to an acetylene. This previously unknown reaction provides a convenient way to construct a large variety of carbocycles and heterocycles. Some reactions envisioned result in the synthesis of exomethylene compounds (equation 6), indenes, benzofurans and indoles (equation 7) and a variety of other compounds.

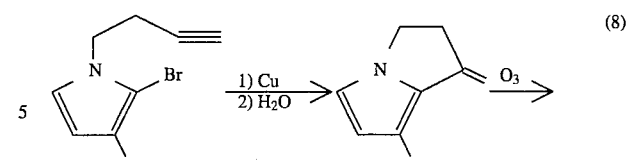  (6)

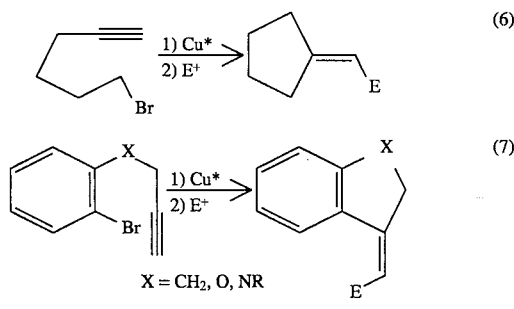  (7)

Some simple natural products are also accessible using this methodology (equations 8 and 9).

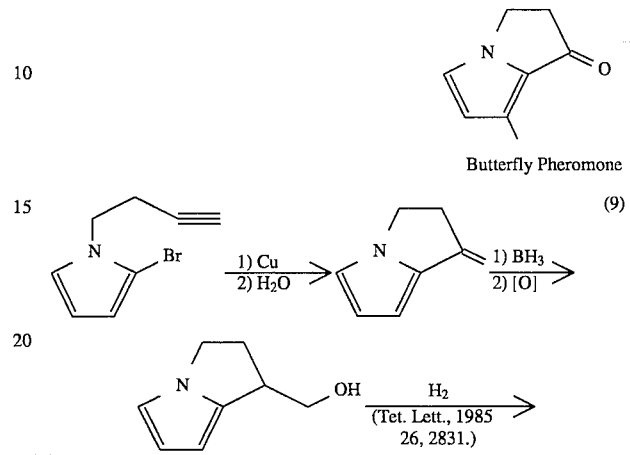

Butterfly Pheromone

Isoretronccanol

Conjugate addition followed by nucleophilic ring closure also provides natural products. The alkylcopper species derived from the copper species is very reactive in conjugate addition reactions with 2-cyclohexenone, giving the 3-alkylated cyclohexanones in generally good to excellent yields. A specific example is shown below. The resulting anolate anion undergoes an addition-elimination cyclization if allowed to.

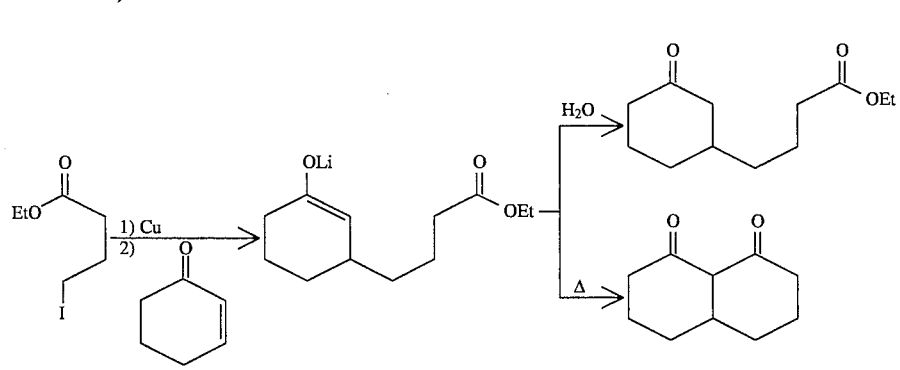

This approach offers the possibility of forming a variety of bicyclic organic systems useful in pharmaceutical arts.

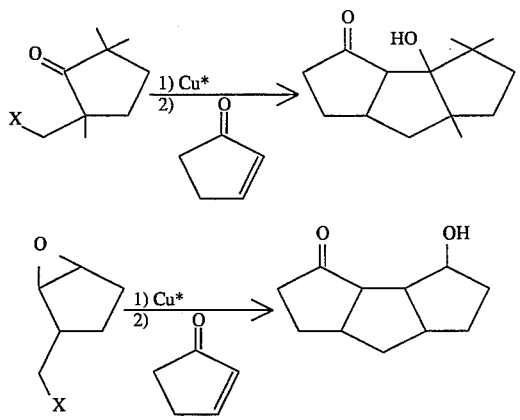

One such important ring skeleton is the above depicted 5-5-5 tricyclic structure. Most naturally occurring condensed tricyclopentanoids are tricyclic sesquiterpenes. Hirsutene, coriolin, hirsutic acid, and capnellene have a linearly-fused tricyclopentane structure. These compounds come from a wide variety of natural sources and many possess significant biological activity such as anticancer activity. In the past two decades, there has been intense activity in the development of synthetic routes to these compounds. The reactions of the organocopper reagents of this invention offer a new, elegant, and effective synthetic approach to these naturally occurring triquinanes.

The invention will be further exemplified with respect to the various specific and preferred embodiments and techniques. It should be understood, however, that many variations and modifications may be made while remaining within the scope of the invention.

Example 1

A representative procedure for the formation of a functionalized organocopper reagent: Li (8.46 mmol) and naphthalene (10.1 mmol) in anhydrous tetrahydrofuran (THF) (15 ml) were stirred under argon until the Li was consumed (approximately 2 h). The flask was then cooled to −100° C. CuCN (8.00 mmol) and LiBr (17.27 mmol) in THF (5 ml) were stirred under argon until the Cu(I) salt was solubilized. The CuCN.2LiBr solution was cooled to −40° C. and transferred into the lithium naphthalide (LiNap) with a cannula. The solution was stirred for 5 min. The active copper solution was warmed to −35° C. and charged with ethyl 4-bromobutyrate (1.95 mmol). (For aryl halides, the solution was warmed to 0° C., immediately charged with aryl halide, and allowed to mix for 1 h.) The solution was stirred for 10 min and was ready for use for acid chloride couplings or conjugate additions.

Example 2

The functionalized organocopper species listed in Table I and prepared according to the procedure of Example 1 can be cross-coupled with benzoyl chloride proceeded smoothly at −35° C. in 30 min to produce the functionalized ketones shown in good to excellent yields (Table I).

To the organocopper species was added benzoyl chloride (3 equiv based on organocopper) neat via syringe at −35° C. The solution was stirred for 30 min, quenched with $NH_4Cl$(satd, 5 ml), and worked up with standard flash silica gel chromatographic techniques.

TABLE I

Cross-Coupling of Benzoyl Chloride with Organocopper Reagents Derived from CuCN.2LiBr-Based Copper

| entry | halide (equiv)[a] | product[b] | % yield[c] |
|---|---|---|---|
| 1 | $Br(CH_2)_7CH_3(0.25)$ | $PhCO(CH_2)_7CH_3$ | 82 |
| 2 | $Br(CH_2)_6Cl(0.25)$ | $PhCO(CH_2)_6Cl^3$ | 80 |
| 3 | $Br(CH_2)_3CO_2Et(0.25)$ | $PhCO(CH_2)_3CO_2Et$ | 81 |
| 4 | $Br(CH_2)_2CO_2Et(0.25)$ | $PhCO(CH_2)_2CO_2Et$ | 43 |
| 5 | $Br(CH_2)_3CN(0.25)$ | $PhCO(CH_2)_3CN$ | 86 |
| 6 | bromobenzene(0.20) | PhCOPh | 87 |
| 7 | $p-BrC_6H_4CN(0.20)$ | $p-NCC_6H_4COPh$ | 60 |
| 8 | $o-BrC_6H_4CN(0.20)$ | $o-NCC_6H_4COPh$ | 74 |
| 9 | $o-BrC_6H_4CO_2Et(0.20)$ | $EtO_2CC_6H_4COPh$ | 51 |
| 10 | $p-BrC_6H_4Cl(0.20)$ | $p-ClC_6H_4COPh$ | 83 |

[a]Based on 1 equiv of CuCN, alkyl halides were allowed to react for 10 min at −35° C. Aryl halides were added at 0° C. and allowed to react for 1 h.
[b]All products gave consistent 1H and $^{13}C$ NMR spectra.
[c]Isolated yields.

The products were easily isolated via flash silica gel chromatography. An excess of acid chloride must be used (generally 2–3 equiv based on organocopper reagent) since unreacted active copper will react with acid chlorides.

Example 3

The organocopper reagents of the invention can also be added to enones as indicated in Table II. The addition of trimethylsilyl chloride (TMSCl) (see, for example, E.J. Corey et al., Tetrahedron Lett., 26, 6015 (1985); E.J. Corey et al., Tetrahedron Lett., 26, 6019 (1985); and A. Alexakis et al., Tetrahedron Lett., 27, 1047 (1986)) to the organocopper reagents made from CuCN·2LiBr-based active copper and the halides listed on Table II allowed for 1,4-conjugate additions to occur readily at −78° C. in good to excellent yields (Table II).

The halide, 0.25–0.30 equiv based on 1 equiv of CuCN, was transferred to the active copper solution at −35° C. After 15 min, the flask was cooled to −78° C. A 2–3 fold excess of TMSCl, in respect to the equivalents of 1,4-adduct, was injected neat into the flask (a 6-fold excess of TMSCl was used for entry 6). The 1,4-adduct was dissolved in THF (10 ml) in a separate vial and delivered dropwise with stirring to the organocopper solution. After 1.5 h at −78° C., the flask was gradually warmed to room temperature.

TABLE II

Conjugate Additions with Organocopper Reagents Derived from CuCN.2LiBr-Based Active Copper

| entry | halide | enone[a] (equiv) | % yield[b] |
|---|---|---|---|
| 1 | $Br(CH_2)_7CH_3$ | A (0.17) | 92 |
| 2 | $Cl(CH_2)_7CH_3$ | A (0.16) | 42 |
| 3 | $Br(CH_2)_3CO_2Et$ | A (0.17) | 70 |
| 4 | $Br(CH_2)_3CO_2Et$ | A (0.12) | 90 |
| 5 | $Br(CH_2)_3CO_2Et$ | B (0.11) | 94 |
| 6 | $Br(CH_2)_3CO_2Et$ | C (0.11) | 87 |
| 7 | $Br(CH_2)_3CN$ | A (0.12) | 87 |
| 8 | $Br(CH_2)_3CN$ | B (0.11) | 92 |
| 9 | $Br(CH_2)_6Cl$ | A (0.12) | 82 |
| 10 | $BrC_6H_{11}$ | A (0.12) | 80 |
| 11 | $BrC_6H_5$ | A (0.11) | 45 |
| 12 | $ClCH_2CH=C(CH_3)_2$ | A (0.10) | 81[c] |

[a]Enone: A = 2-cyclohexen-1-one, B = 4-hexen-3-one. C = trans-cinnamaldehyde.
[b]Isolated yield of 1,4-conjugate addition product (not shown). All products gave consistent IR, HRMS, and $^1H$ and $^{13}C$ NMR spectra.
[c]The enone was injected neat at −90° C.
(3-Methyl-2-butenyl)cyclohexanone was the sole product isolated.

Both cyclic and acyclic enones can be used with the ideal organocopper to enone ratio being approximately 2.5:1, respectively. These functionalized organocopper reagents also add to α,β-unsaturated aldehydes in the presence of TMSCl to afford highly functionalized aldehydes (see entry 6 in Table II). The competitive 1,2-addition was not seen by GC analysis.

Example 4

The active copper reagent reacts with allylic chlorides to form the corresponding allylic organocopper species. The resulting organocopper reagents were trapped with benzoyl chloride to produce the ketones shown in Table III.

To a solution of active copper at −100° C. was added the allyl chloride (0.25 equiv) which was previously cooled to −78° C. in a vial admixed with THF (1 ml). The PhCOCl (3 equiv based on organocopper) was added neat via syringe at −100° C. and allowed to react for 15 min.

TABLE III

Reaction of Allyl Organocopper Reagents
Derived from CuCN.2LiBr with Benzoyl Chloride

| entry | allyl chloridea | PhCORb | % yieldc |
|---|---|---|---|
| 1 | ClCH$_2$CH=CH$_2$ | PhCOCH$_2$CH=CH$_2$ | 65 |
| 2 | AcOCH$_2$CH=CH$_2$ | PhCOCH$_2$CH=CH$_2$ | 63 |
| 3 | ClCH$_2$C(CH$_3$)=CH$_2$ | PhCOCH$_2$C(CH$_3$)=CH$_2$ | 75 |
| 4 | CH$_3$CH(Cl)CH=CH$_2$ | PHCOCH(CH$_3$)CH=CH$_2$ | 72 |
| 5 | ClCH$_2$CH=C(CH$_3$) | PHCOC(CH$_3$)$_2$CH=CH$_2$ | 74 | aAll products had consistent $^1$H, $^{13}$C, and $^{13}$C DEPT NMR spectra.
bIsolated yields.

Unsymmetrical allyl chlorides presumably yield the primary organocopper reagent upon reaction with active copper. Since the 1,4-conjugate addition of prenylcopper with cyclohexanone proceeded via α attack (Table II, entry 12), reaction of prenylcopper with benzoyl chloride must involve γ attack (Table III, entry 5). This is the first reported formation of an allyl organocopper reagent formed directly from an allyl chloride and acetate.

Example 5

The reaction of the active copper species with functionalized allylic chlorides produces the first known, preformed functionalized allylic organocuprate reagents. These allylic cuprate reagents can contain ketone, alpha,beta-unsaturated ketone, ester, epoxide, and nitrile functionalities. The resulting allylic cuprates react with a variety of electrophiles to produce highly functionalized organic products, Table IV.

The functionalized allyl chloride (0.4 equiv.) is admixed in 4 ml of THF, cooled to −78° C., and added to the active copper solution at −100° C. and allowed to stir for 10 min. The electrophile (0.2 equiv.) is admixed in 2 ml of THF, and added to the organocuprate at −90° C. and allowed to warm to −20° C. over the course of two to three hours.

TABLE IV $$\text{Cu*} + R_F\diagup\!\!\!\diagdown\!\!\!\diagup Cl \xrightarrow[10 \text{ min.}]{-100° C.} \xrightarrow[-90° \text{ to } -20° C.]{E^+} R_F\diagup\!\!\!\diagdown\!\!\!\diagup E$$
1.0 eq.

| Allyl Chloride | (eq.) | E$^+$ | (eq.) | Product | Isolated Yield |
|---|---|---|---|---|---|
| [structure: 4-(1-chloromethyl-vinyl)cyclohexanone] | (.4) | PhCHO | (.2) | [structure: with OH, Ph] | 94% |
| [structure: 4-(1-chloromethyl-vinyl)cyclohexanone] | (.4) | PhCOCH$_3$ | (.2) | [structure: with OH, Ph] | 90% |
| [structure: 5-chloro-6-methyl-hept-6-en-2-one] | (.4) | PhCHO | (.2) | [structure: with OH, Ph] | 62% |

TABLE IV-continued

| Allyl Chloride | (eq.) | E+ | (eq.) | Product | Isolated Yield |
|---|---|---|---|---|---|
| [cyclohexenone with allyl chloride substituent] | (.4) | PhCHO | (.2) | [cyclohexenone with CH(OH)Ph product] | 67% |
| [chloroallyl acetate chain] | (.35) | PhCOCl | (1.0) | [ketone product with OCCH₃] | 70% |
| [chloroallyl acetate chain] | (.4) | NCH₂Ph ‖ PhCH | (.2) | [HNCH₂Ph product with OCCH₃] | 79% |
| [chloroallyl nitrile chain] | (.4) | PhCHO | (.2) | [OH-Ph product with CN] | 89% |

EXAMPLE 6

The reaction of 2-chloroallyl acetate with active copper derived from CuCN·LiCl allows for the formation of the biscuprate (1)(scheme 1). Since the allylic organocopper moiety is more reactive than the vinyl copper moiety, one can selectively add an electrophile to the allylic segment then add another electrophile to the vinyl copper segment.

Thus, to a solution of active copper (1 equiv.) is added 2-chloroallyl acetate (0.25 equiv.) at −100° C. for 20 minutes producing the biscuprate (1). The reaction of (1) with benzaldehyde at −78° C. followed by addition of $I_2$ allowed for the production of (2) in good yield.

Scheme 1

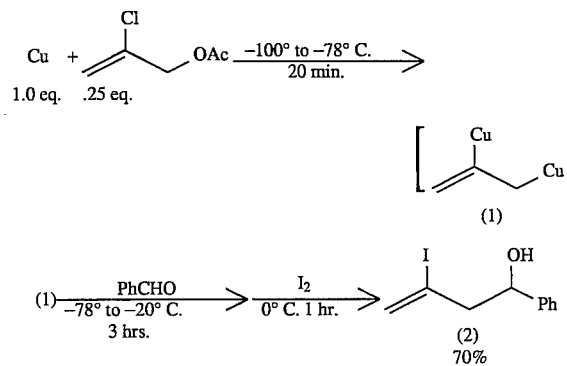

TABLE V

Bis Organocopper and Propargyl Reagents

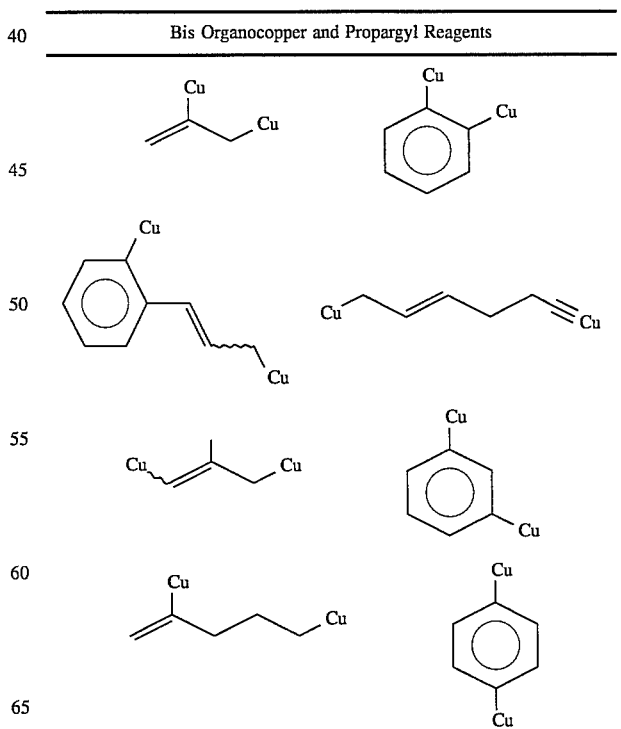

TABLE V-continued
Bis Organocopper and Propargyl Reagents

R1, R2, R3 = H, alkyl, aryl, etc.

[1]If bis complexes are formed on identical hybrized carbons, two identical electrophiles can be used.
[2]If bis copper complexes are formed on different hybridized carbons, electrophiles can be selectively added.

TABLE VI
Intramolecular Organocopper Reactions

A. Preparation of ketone and aldehyde containing cuprates which will undergo 1.2 addition reactions to form novel cyclic molecules.

B. Other examples:

C. Other examples involving epoxides.

optically pure epoxide cuperates → optically pure carbocycles*

TABLE VI-continued

Intramolecular Organocopper Reactions

D. Intramolecular 1,4 Conjugate Additions

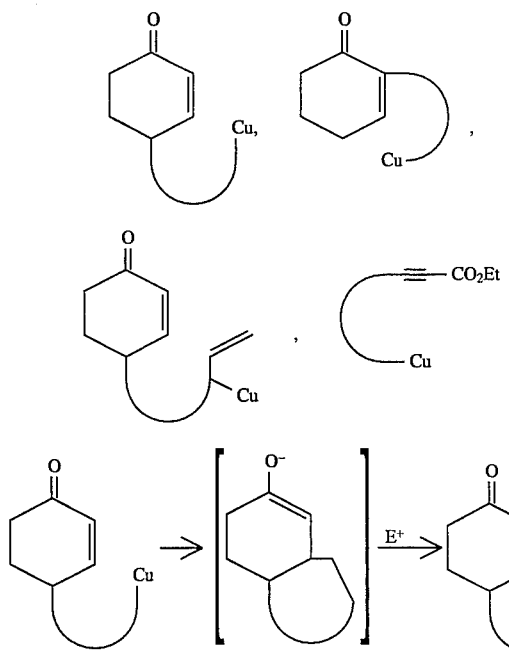

E. Intramolecular Reactions with bis-organocuprates

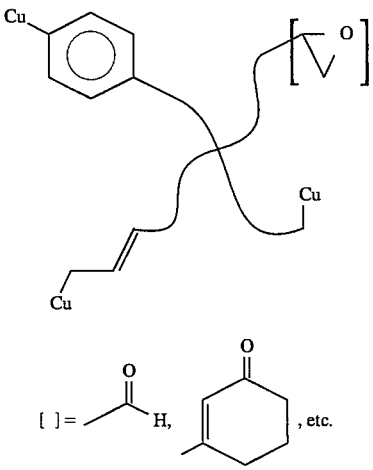

*This would be a general approach to chiral substrates which is of a major concern to drug companies today.

What is claimed is:

1. A zerovalent copper species consisting essentially of a combination of zerovalent copper atoms and an alkali metal salt of halide and an alkali metal salt of a cyanide; wherein the copper species is capable of reacting with an allylic halide or acetate to form an allylic organocuprate.

2. The zerovalent copper species of claim 1 wherein the allylic halide or acetate contains at least one functional moiety selected from a group consisting of a ketone, an alpha,beta-unsaturated ketone, an ester, an epoxide, and a nitrile.

3. The zerovalent copper species of claim 1 wherein the alkali metal salt of cyanide is selected from a group consisting of lithium cyanide, sodium cyanide, and potassium cyanide.

4. The zerovalent copper species of claim 3 wherein the zerovalent copper atoms are in combination with lithium cyanide and a lithium halide.

5. A zerovalent copper species consisting essentially of a combination of formally zerovalent copper atoms and an alkali metal salt of halide and an alkali metal salt of a cyanide; wherein the copper species is capable of reacting with a compound of the formula RC(0)X to form a compound of the formula RC(0)Cu, wherein R is a $C_{1-20}$ alkyl or a $C_{1-20}$ aryl and X is a halide.

6. A zerovalent copper species consisting essentially of a combination of formally zerovalent copper atoms and an alkali metal salt of halide and an alkali metal salt of a cyanide; wherein the copper species is capable of deoxygenating a fulfoxide, a sulfone, or a sulfonate.

7. A zerovalent copper species consisting essentially of a combination of formally zerovalent copper atoms and an alkali metal salt of halide and an alkali metal salt of a cyanide; wherein the copper species is:

(a) capable of reacting with an alkyl, allylic, vinyl or phenyl halide or acetate to produce the corresponding organocuprate with less than about 1% of a homocoupled byproduct;

(b) free of phosphines; and (c) highly dispersible in ethereal, polyethereal, or hydrocarbon solvents.

8. The zerovalent copper species of claim 7 wherein the alkali metal salt of cyanide is selected from a group consisting of lithium cyanide, sodium cyanide, and potassium cyanide.

9. The zerovalent copper species of claim 8 wherein the zerovalent copper metal atoms are in combination with lithium cyanide and a lithium halide.

10. The zerovalent copper species of claim 9 wherein the lithium halide is selected from a group consisting of lithium bromide and lithium chloride.

* * * * *

UNITED STATES PATENT AND TRADEMARK OFFICE
CERTIFICATE OF CORRECTION

PATENT NO. : 5,490,951

DATED : February 13, 1996

INVENTOR(S) : Reuben D. Rieke

It is certified that error appears in the above-identified patent and that said Letters Patent is hereby corrected as shown below:

On column 1, line 59, please delete "cupwates" and substitute therefore --cuprates--

On column 3, line 41, please insert --Generally, the reducing agent may be any-- after the letters "Li"

On column 5, line 10, please delete "either" and substitute therefore --ether--

On column 17, line 52, please insert pages 26, 27 and 28 after the word "today"

--

26

TABLE VII
Aryl & Alkylaryl Copper Reagents

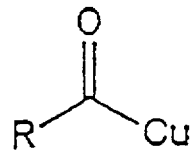

R is alkyl or aryl such as $C_1$ to $C_{20}$ alkyl, phenyl, naphthyl or benzyl.

UNITED STATES PATENT AND TRADEMARK OFFICE
CERTIFICATE OF CORRECTION

PATENT NO. : 5,490,951

DATED : February 13, 1996

INVENTOR(S) : Reuben D. Rieke

It is certified that error appears in the above-identified patent and that said Letters Patent is hereby corrected as shown below:

TABLE VIII
Deoxygenation of Sulfides, Sulfones and Sulfonates

A)

B) 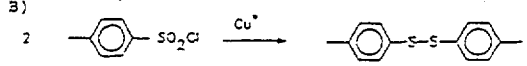

C) 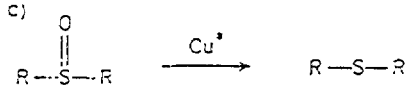

D) 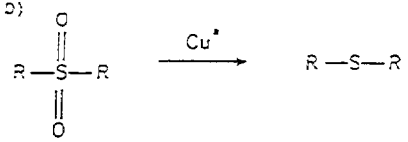

E) 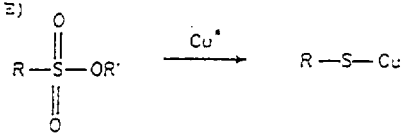

UNITED STATES PATENT AND TRADEMARK OFFICE
CERTIFICATE OF CORRECTION

PATENT NO. : 5,490,951

DATED : February 13, 1996

INVENTOR(S) : Reuben D. Rieke

It is certified that error appears in the above-identified patent and that said Letters Patent is hereby corrected as shown below:

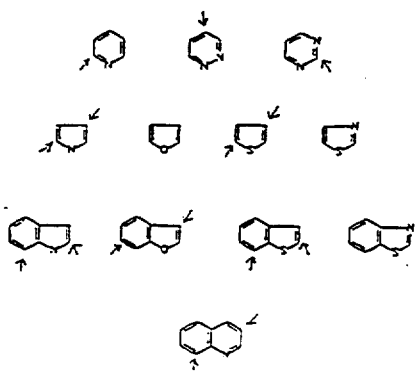

UNITED STATES PATENT AND TRADEMARK OFFICE
CERTIFICATE OF CORRECTION

PATENT NO. : 5,490,951
DATED : February 13, 1996
INVENTOR(S) : Reuben D. Rieke

It is certified that error appears in the above-indentified patent and that said Letters Patent is hereby corrected as shown below:

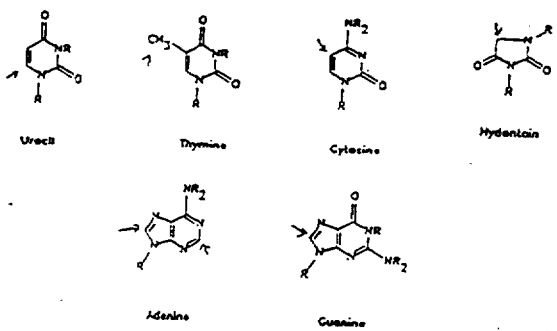

The copper can be substituted at any position capable of being substituted by a halogen. Some examples of such copper substitutions are indicated by arrows on the above structure.

Signed and Sealed this

Sixteenth Day of July, 1996

Attest:

BRUCE LEHMAN

Attesting Officer

Commissioner of Patents and Trademarks